(12) United States Patent
Klanow et al.

(10) Patent No.: US 9,254,071 B2
(45) Date of Patent: Feb. 9, 2016

(54) ARENA CLEANER MACHINE AND METHOD FOR CLEANING AN ARENA

(71) Applicant: ArenaServ LLC, Canton, MI (US)

(72) Inventors: Brian Klanow, Holly, MI (US); Patrick J. Sieloff, Superior Township, MI (US)

(73) Assignee: ArenaServ LLC, Canton, MI (US)

( * ) Notice: Subject to any disclaimer, the term of this patent is extended or adjusted under 35 U.S.C. 154(b) by 491 days.

(21) Appl. No.: 13/749,904

(22) Filed: Jan. 25, 2013

(65) Prior Publication Data

US 2013/0192636 A1 Aug. 1, 2013

Related U.S. Application Data

(60) Provisional application No. 61/592,118, filed on Jan. 30, 2012.

(51) Int. Cl.
| | | |
|---|---|---|
| B08B 7/00 | (2006.01) |
| A47L 11/14 | (2006.01) |
| A61B 1/018 | (2006.01) |
| A61B 1/24 | (2006.01) |
| A61B 1/273 | (2006.01) |
| A61B 1/303 | (2006.01) |
| A61B 1/31 | (2006.01) |
| A61B 1/313 | (2006.01) |
| A61B 5/00 | (2006.01) |
| A61B 5/06 | (2006.01) |
| A61B 6/12 | (2006.01) |
| A61B 6/00 | (2006.01) |
| A61B 8/08 | (2006.01) |
| A61B 17/00 | (2006.01) |
| A61N 5/10 | (2006.01) |
| A47L 11/38 | (2006.01) |
| B08B 1/04 | (2006.01) |
| A46B 13/00 | (2006.01) |

(52) U.S. Cl.
CPC ............. *A47L 11/145* (2013.01); *A46B 13/008* (2013.01); *A47L 11/38* (2013.01); *A61B 1/018* (2013.01); *A61B 1/24* (2013.01); *A61B 1/2733* (2013.01); *A61B 1/303* (2013.01); *A61B 1/31* (2013.01); *A61B 1/3132* (2013.01); *A61B 5/0091* (2013.01); *A61B 5/064* (2013.01); *A61B 5/4244* (2013.01); *A61B 5/4312* (2013.01); *A61B 5/4381* (2013.01); *A61B 6/12* (2013.01); *A61B 6/502* (2013.01); *A61B 8/0841* (2013.01); *A61B 17/00234* (2013.01); *A61N 5/1039* (2013.01); *B08B 1/04* (2013.01)

(58) Field of Classification Search
None
See application file for complete search history.

(56) References Cited

U.S. PATENT DOCUMENTS

| | | | | |
|---|---|---|---|---|
| 3,869,749 A | * | 3/1975 | London ................. | A47L 11/302 15/302 |
| 4,835,811 A | * | 6/1989 | Crowhurst .............. | A47L 11/38 15/56 |
| 2010/0229891 A1 | * | 9/2010 | Goff ...................... | A47L 11/302 134/6 |

* cited by examiner

*Primary Examiner* — Eric Golightly
(74) *Attorney, Agent, or Firm* — Carlson, Gaskey & Olds

(57) ABSTRACT

An arena cleaning machine includes cleaning members, such as pads or brushes supported on a carriage that provides stability to the cleaning members and situates them in a position to contact the surface of ice rink dasher boards. The cleaning members are moveable into a desired cleaning position by adjusting their position along the carriage. A driver of the machine can make several passes around the rink, cleaning successive strips on the dasher boards.

10 Claims, 3 Drawing Sheets

ARENA CLEANER MACHINE AND METHOD FOR CLEANING AN ARENA

CROSS REFERENCE TO RELATED APPLICATION

This application claims priority to U.S. Provisional Application No. 61/592,118 which was filed on Jan. 30, 2012.

BACKGROUND

Sports arenas are prone to wear and tear from hosting various sporting events. This is especially true of hockey arenas where skates, sticks and pucks frequently contact the dasher boards surrounding the ice rink. After a number of hockey games, scuff marks will appear and dirt and debris will begin to accumulate in grooves and gouges on the dasher boards. Over time the dasher boards look dirty, worn and unsightly with black scuff marks all over the white boards. Additionally, dasher boards can accumulate germs and other bacteria if they are not routinely cleaned.

It is desirable to frequently clean and polish the dasher boards. However, cleaning and polishing the dasher boards is a time consuming process due to the size of a hockey arena and the amount of wear and tear the dasher boards sustain. It is also difficult to remove many of the scuff marks as they are typically black

SUMMARY

In an example embodiment, an arena cleaner machine includes a motorized vehicle. A carriage is supported for movement with the vehicle. The carriage includes at least one vertically arranged support member that is spaced from the vehicle. A cleaning member assembly includes a frame portion that is supported by the carriage, a first cleaning member supported by the frame portion and a second cleaning member supported by the frame portion. The frame portion has at least one frame member that is moveable along the vertically arranged support member for selecting a vertical position of the cleaning members, which are each selectively moveable relative to the frame portion. A mover is configured to selectively cause movement of the frame member along the support member. A first motor is associated with the first cleaning member for causing cleaning movement of the first cleaning member. A second motor is associated with the second cleaning member for causing cleaning movement of the second cleaning member. A pressurized fluid storage tank is supported on the vehicle. A plurality of nozzles are situated near the cleaning members. A valve assembly is selectively controllable for directing fluid from the storage tank through the nozzles.

The various features of a disclosed example can be best understood from the following description and the accompanying drawings, which can be briefly described as follows.

DETAILED DESCRIPTION

Figure 1:
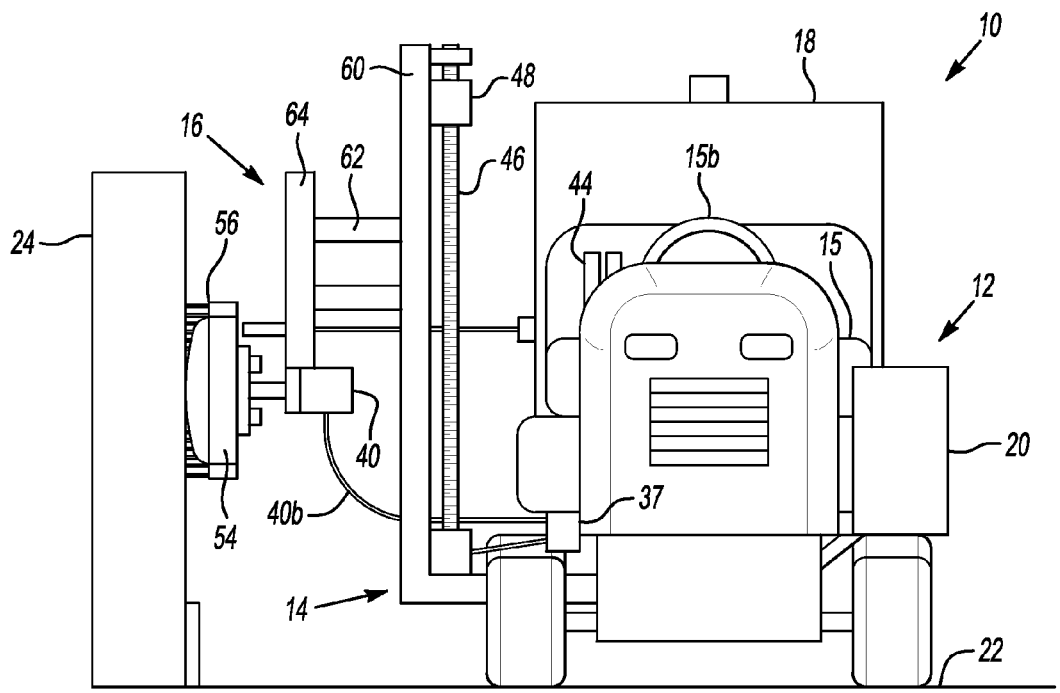
FIG. 1 illustrates a front view of an example arena cleaner machine.

FIGS. 1-4 show an example arena cleaner machine 10. FIG. 1 illustrates a front view of the example arena cleaner machine 10 including a base vehicle 12. In one particular example, the base vehicle 12 comprises a tractor, such as an eighteen horsepower tractor. The cleaner machine 10 also has a carriage assembly 14, a brush assembly 16 supported on the carriage assembly 14, a fluid tank 18 and a hydraulic fluid reservoir 20. In this example, the arena cleaner machine 10 is configured to travel on an arena floor surface 22, such as an ice rink, while the brush assembly 16 cleans and polishes an arena wall 24, such as the dasher boards.

Figure 2:
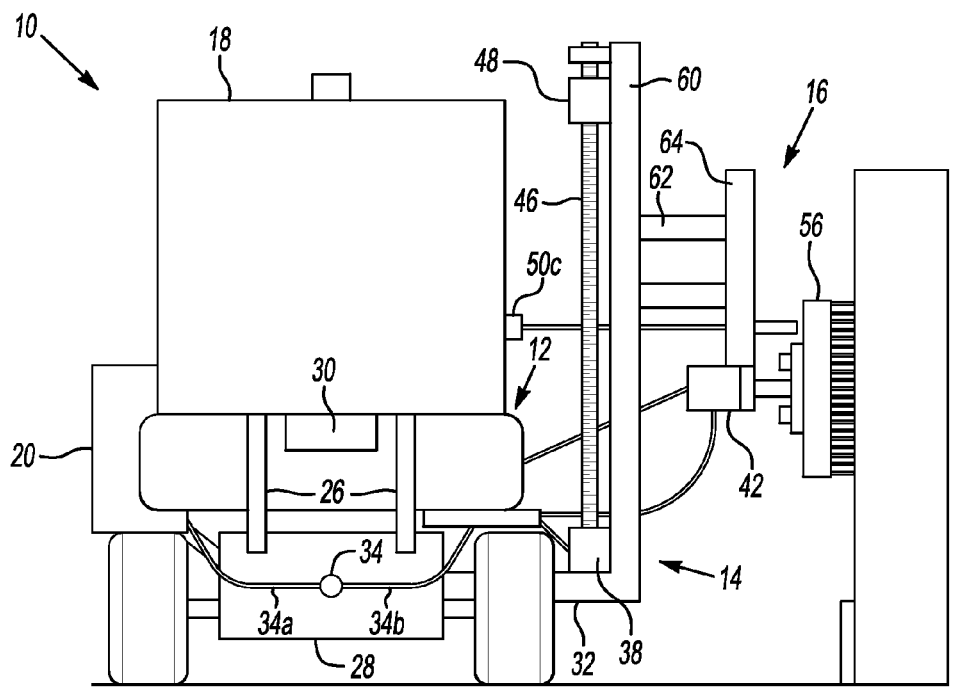
FIG. 2 illustrates a rear view of the example arena cleaner machine of FIG. 1.

As best seen in FIG. 2, the fluid tank 18 is attached to a rear portion of the base vehicle 12 and supported by braces 26 that extend from the fluid tank 18 to a frame 28 of the base vehicle 12. The example fluid tank 18 stores approximately forty-five gallons of a fluid useful for dasher board cleaning, such as warm water for rinsing down the boards. A compressor 30 is located below the fluid tank 18 and is in fluid communication with and pressurizes the fluid tank 18. Although the compressor 30 is located beneath the fluid tank 18 in this particular example, one of ordinary skill in the art would recognize that the compressor 30 could be located remotely from the fluid tank 18.

FIGS. 1, 2, 4 and 6 illustrate the example carriage assembly 14. The carriage assembly 14 supports the weight of the brush assembly 16 and is structurally capable of withstanding the forces associated with using the brush assembly 16 to clean the arena wall 24. Given that hockey rinks are quite large, it is useful to have large sized cleaning members 54 and 56 to minimize the number of passes that must be made to clean the entire surface of the dasher boards around the entire ice surface. One example carriage assembly 14 comprises steel tubes having a square cross-section to support the cleaning members and their associated motors.

The carriage assembly 14 also provides an ability to adjust a position of the brush assembly 16 so that different portions of the dasher boards 24 may be cleaned during successive passes around the rink. For example, the top of the boards 24 (e.g., about 18 inches or 0.5 meters) may be cleaned during a first pass followed by the next segment below that on a subsequent pass. The carriage assembly 14 is attached to the base vehicle 12 by mounting arms 32. In this example, the mounting arms 32 are secured to the base vehicle frame 28. The carriage assembly 14 includes a carriage motor 38, which is a hydraulic motor in one example, that raises and lowers the brush assembly 16 relative to the arena floor 22. The carriage hydraulic motor 38 is attached to a rotatable screw 46 which engages a threaded member 48 located on the brush assembly 16. When the carriage hydraulic motor 38 rotates the rotatable screw 46 in a first direction, the distance between the brush assembly 16 and the arena floor 22 increases (e.g., the brush assembly 16 moves up). When the carriage hydraulic motor 38 rotates the rotatable screw 46 in a second opposite direction, the distance between the brush assembly 16 and the arena floor 22 decreases (e.g., the brush assembly 16 moves down). The vertical movement of the brush assembly 16 allows the arena cleaner machine 10 to engage a particular vertical portion (e.g., a strip having a vertical width) of the arena wall 24. Moving the brush assembly 16 into different positions on successive passes around the arena facilitates cleaning a strip during each pass until the entire arena wall 24 has been cleaned.

A first hydraulic motor 40 rotates the first cleaning member 54 and a second hydraulic motor 42 rotates the second cleaning member 56. In one example, the first cleaning member 54 includes an abrasive pad and the second cleaning member 56 includes a bristle brush, such as a nylon bristle brush, for removing scuff marks and dirt and debris from grooves or gouges in the arena wall 24. When the arena cleaner machine 10 is used to remove scuff marks and dirt and debris, the arena wall 24 is sprayed with a cleaning solution to aid in removing the scuff marks and dirt and debris prior to being engaged by the first cleaning member 54 and the second cleaning member 56.

In another example, the first cleaning member 54 and the second cleaning member 56 include polishing pads and the arena wall 24 is sprayed with a wax prior to polishing with the first cleaning member 54 and the second cleaning member 56 to seal and protect the arena wall 24.

Figure 4:
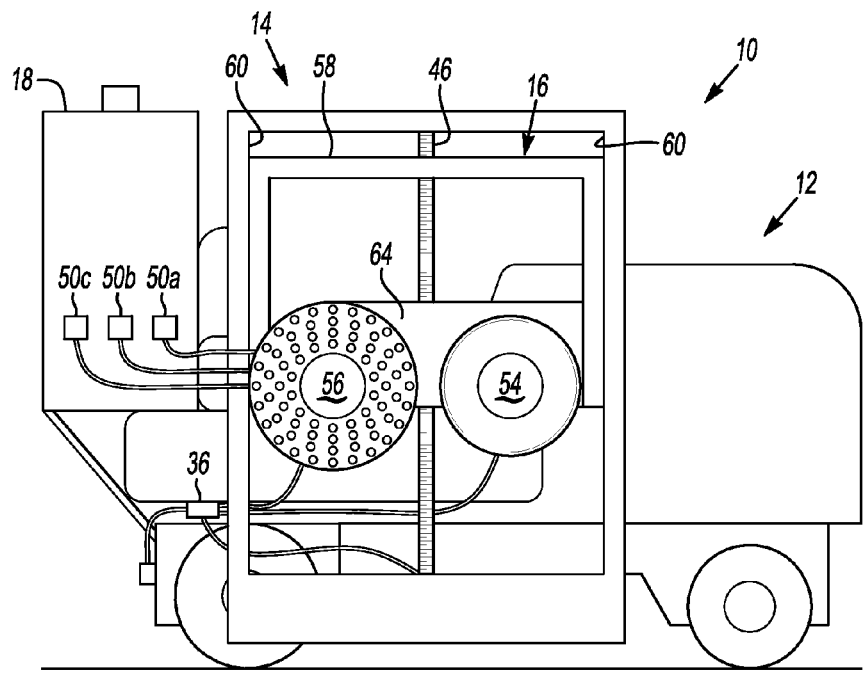
FIG. 4 illustrates a side view of the example arena cleaner machine of FIG. 1.

As best seen in FIG. 4, the brush assembly 16 includes a rectangular frame member 58 that is moveable along vertical rails 60 on the carriage assembly 14. The threaded member 48 (FIG. 5) is attached to the frame member 58 to facilitate raising and lowering the brush assembly 16 relative the arena floor 22 as the rotatable screw 46 is rotated by the carriage hydraulic motor 38 (FIG. 2). In this example, the vertical rails 60 are vertically oriented support members that establish a vertical path for moving a frame of the brush assembly 16 up and down as needed. The frame member 58 in this example is received between the vertical rails 60 and is slidable along those rails responsive to rotation of the threaded member 46. The carriage 14 is structurally stable enough to provide vertical, horizontal and rotational stability to the brush assembly 16. The structural stability of the carriage 14 allows a driver to position the vehicle 12 a desired distance from the dasher boards 24 without having to compensate for unexpected or undesired movement or deflection of the cleaning members relative to the vehicle 12.

The structural support provided to the brush assembly 16 is based on a rigid connection between the vehicle and the carriage 14. The illustrated arrangement is superior to one that relies upon an extending arm with a brush supported near the end of the arm. The entire weight of the vehicle is useable for maintaining a desired position of the cleaning members 54 and 56 relative to the board surface that is being cleaned. The illustrated arrangement makes it easier for an operator to complete a cleaning process and reduces the chances for operator error that may otherwise result in inconsistent or less than satisfactory cleaning of the board surface.

Figure 5:
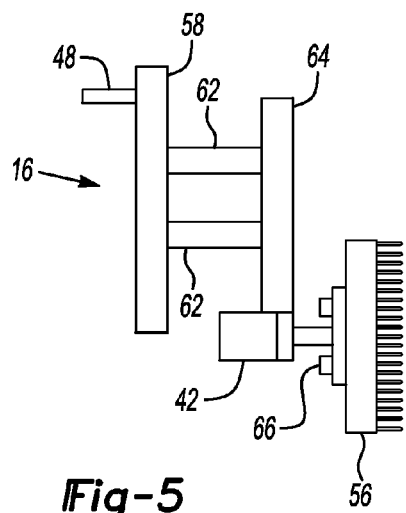
FIG. 5 illustrates selected portions of an example brush assembly.
Figure 6:
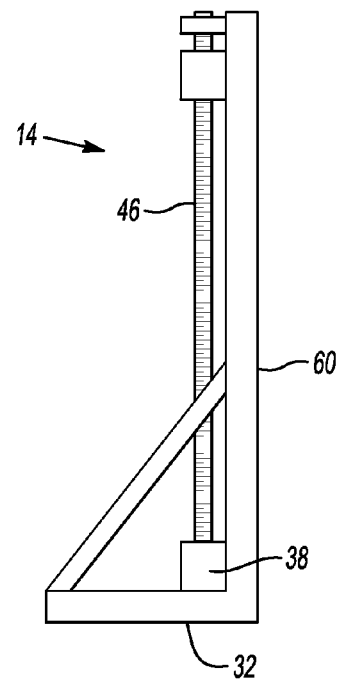
FIG. 6 illustrates selected portions of an example carriage assembly.

FIG. 5 illustrates selected portions of the brush assembly 16. Arms 62 connect the frame member 58 to a generally rectangular brush frame 64. The second hydraulic motor 42 is attached to the brush frame 64. Brush angle adjusters 66, such as bolts, are located adjacent the second cleaning member 56. In one example, the brush angle adjusters 66 may be turned in a first direction from a neutral position, where the axis of the second cleaning member 56 is perpendicular to a plane formed by the brush frame 64, to a position where the axis of the second cleaning member 56 is at an oblique angle relative to the brush frame 64. The brush angle adjusters 66 may also be turned in a second opposite direction until the axis of the second cleaning member 56 points at an oppositely facing oblique angle relative to the brush frame 64. Additional brush angle adjusters 66 function in a similar manner to allow a selected orientation of the first cleaning member 54. Adjusting the angle or tilt of the first cleaning member 56 and the second cleaning member 54 allows for better cleaning action and accommodates for various surface configurations or irregularities in the arena walls 24 or variations in the cleaning members 54, 56, themselves.

Figure 7:
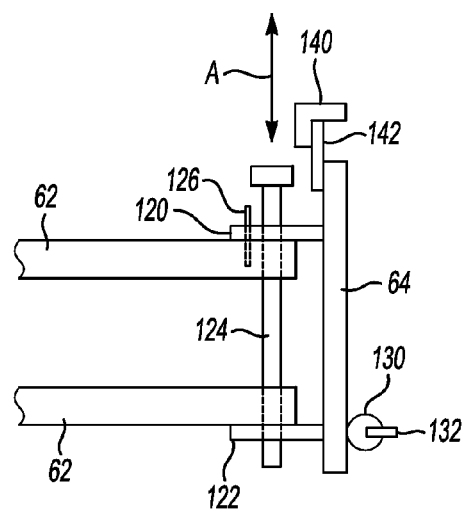
FIG. 7 is a side view illustration of an example mounting plate that is useful with one embodiment of a brush assembly.
Figure 8:
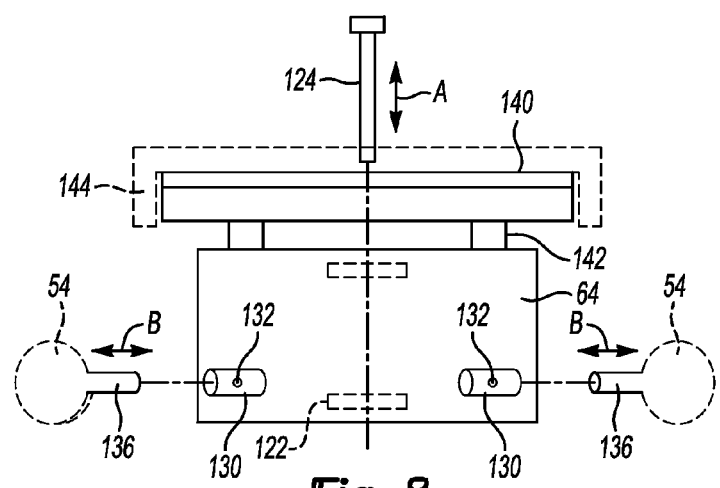
FIG. 8 is a front view illustration of selected features of a brush assembly that includes the example plate of FIG. 7.

FIGS. 7 and 8 illustrate another embodiment of a brush or cleaning member assembly 16. In this example, a mounting plate 64 is selectively secured to the arms 62, which are part of the frame portion that is supported by the carriage 14. The plate 64 in this example includes mounting tabs 120 and 122 that are received against the arms 62, respectively. A post or pin 124 is received through a hole in the mounting tabs 120 and 122 and the arms 62 for securing the tabs and the plate 64 to the arms 62. The post or pin 124 is selectively removable as schematically indicated by the arrow A so that the plate 64 may be removed and replaced with a different plate configuration, for example. The illustrated example includes a locking pin 126 that is received through a hole in the tab 120 and the corresponding arm 62 to prevent the plate 64 from pivoting about the post 124.

Another feature of the example plate 64 is that it includes mounting sleeves 130 and locking members 132 that are configured to support cleaning members, such as brushes or pads, on the plate 64. FIG. 8 schematically shows corresponding portions 136 of cleaning members 54 and 56 that are selectively inserted into or removed from the mounting sleeves 130 as schematically represented by the arrows B. The locking members 132 may be pins or bolts that hold the portions 136 of the cleaning members in place within the mounting sleeves 130.

The arrangement shown in FIGS. 7 and 8 facilitates easy changes of cleaning members or entire brush assemblies, which facilitates more efficient arena cleaning processes. With the illustrated example, the brush assembly or cleaning members may be changed to accommodate differing needs at a job site in a matter of seconds rather than minutes, which saves labor time and expense.

Another feature of the arrangement shown in FIGS. 7 and 8 is that it includes a L-shaped bracket 140 supported on extensions 142 that are secured to the plate 64. A cover element, such as a brush or shroud schematically shown at 144, may be secured to and supported on the L-shaped bracket 140. A cover element may be useful for cleaning a portion of a wall or side board surface above the location of the cleaning members 54 and 56 or it may be useful for containing any overspray of liquid applied during the cleaning process.

In an example ice arena cleaning method, a cleaning solution is sprayed on the dasher boards 24 with a manual sprayer (not illustrated) to aid in dissolving accumulated scuff marks and dirt. An individual may walk along the dasher boards 24 while spraying the cleaning solution on them, for example. Once the cleaning solution has been applied and allowed to set for a desired time, the arena cleaner machine 10 is driven around the rink adjacent the dasher boards 24 with the brush assembly 16 positioned to allow the first cleaning member 54 and the second cleaning member 56 to engage the dasher boards 24. The first cleaning member 54 leads the second cleaning member 56 as the machine 10 travels along the boards.

The controls 44 allow the driver to manipulate the position of the brush assembly 16 on the carriage assembly 14 to position the cleaning members 52 and 56 to clean a top portion of the dasher boards as the arena cleaner machine 10 travels on the ice or floor during a first pass along the boards.

The controls 44 and the manner in which the cleaning members 52 and 56 are supported for movement along the carriage 14 allow for a driver to conveniently and accurately adjust the position of the cleaning members at any time during a cleaning procedure.

While the cleaning members 54, 56 are rotating, the nozzles 52a, 52b and 52c spray a rinsing solution on the forward and rear portions of the first and second cleaning members 54 and 56. One pass around the rink results in a clean strip about the height of the diameter of the cleaning members (e.g., 18 inches or 0.5 meters) around the dasher boards.

The first and second cleaning members 54 and 56 are lowered to a position just beneath the most recently cleaned strip after each pass around the arena. With each pass, another section of the dasher boards, which is below the section cleaned on the previous pass, gets cleaned until the entire arena wall has been cleaned. In one example, the cleaning members have a diameter that is about one-half the height of the dasher boards so two passes around the rink is sufficient to clean the entire boards.

In one example, after the dasher boards 24 have been cleaned, a protectant, such as wax, is applied to the dasher boards 24 with a manual sprayer (not illustrated). Polishing pads are attached to the first and second cleaning members 54 and 56 to polish the dasher boards as the machine 10 is driven around the rink several times with the pads at a different height each pass. When a wax or other protectant is applied in this manner the valves 50a-c are kept closed to avoid spraying any liquid onto the dasher boards during buffing.

Figure 3:
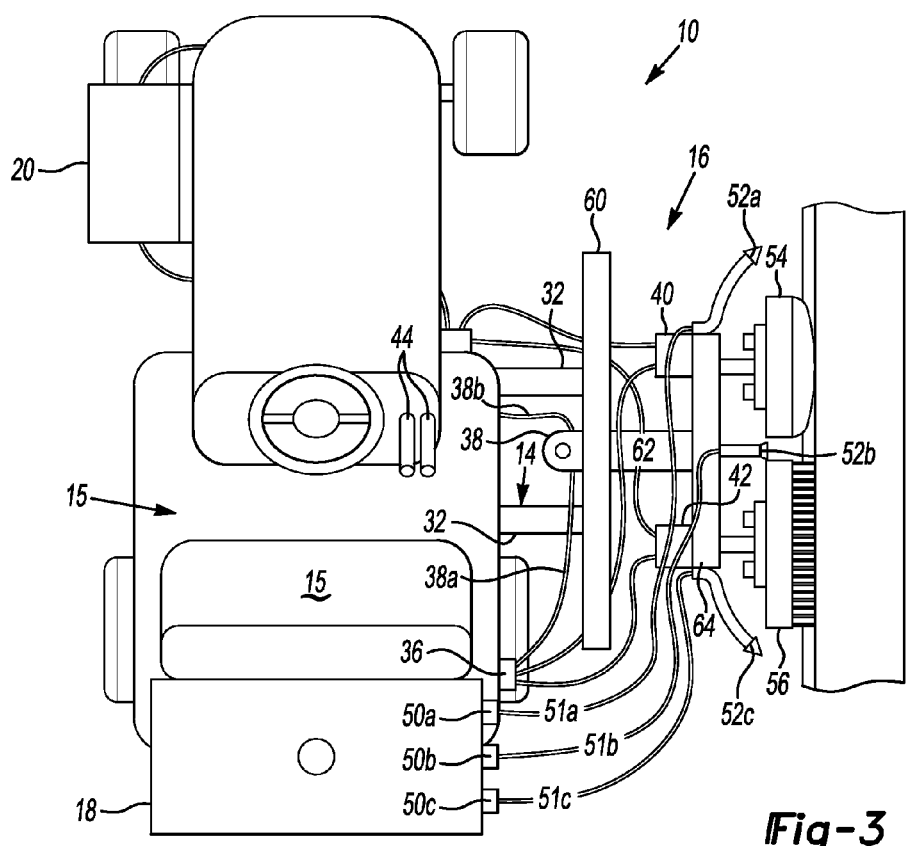
FIG. 3 illustrates a top view of the example arena cleaner machine of FIG. 1.

FIG. 3 illustrates a top view of the arena cleaner machine 10 and shows an example arrangement for controlling fluid flow during a cleaning procedure. A first fluid line 51a extends between a first valve 50a and a first nozzle 52a. A second fluid line 51b extends between a second valve 50b and a second nozzle 52b. A third fluid line 51c extends between a third valve 50c and a third nozzle 52c. In this example, the first valve 50a, the second valve 50b and the third valve 50c are ball valves. Other example embodiments include a different type of valve.

The valves 50a, 50b and 50c allow a user or driver to control distribution of cleaning or rinsing fluid while the user is seated in a driver seat 15 in this example. Opening the first valve 50a allows fluid to flow from the fluid tank 18 to the first nozzle 52a located in front of and substantially vertically aligned with the first cleaning member 54, which may be an abrasive cleaning pad, a buffing pad or a bristle brush.

Opening the second valve 50b allows fluid to flow from the fluid tank 18 to the second nozzle 52b located between the first cleaning member 54 and a second cleaning member 56, which also may be an abrasive cleaning pad, a buffing pad or a bristle brush. In one particular example, the first cleaning member 54 comprises an abrasive cleaning pad and the second cleaning member 56 comprises a bristle brush.

A driver or user can selectively open the third valve 50c to allow fluid to flow from the fluid tank 18 to the third nozzle 52c located behind and substantially vertically aligned with the second cleaning member 56. In this example, the first nozzle 52a, the second nozzle 52b, and the third nozzle 52c are adjustable to allow a user to manipulate the nozzle spray direction based on use. For example, the nozzles 52a, 52b and 52c could be positioned to spray directly onto the arena wall 24 or onto either of the first cleaning member 54 or the second cleaning member 56.

The preceding describes at least one example embodiment in illustrative rather than limiting terms. Variations and modifications to the disclosed example embodiments may become apparent to those skilled in the art that come within the scope of legal protection provided by the following claims. Therefore, the claims must be studied to determine the scope of legal protection.

We claim:

1. An arena cleaner machine, comprising:
 a motorized vehicle;
 a carriage supported for movement with the vehicle, the carriage including at least one vertically arranged support member that is spaced from the vehicle, wherein the carriage is located transverse to a forward or reverse direction of the vehicle;
 a cleaning member assembly including
  a frame portion that is supported by the carriage,
  a first cleaning member supported by the frame portion and
  a second cleaning member supported by the frame portion, the frame portion having at least one frame member that is moveable along the vertically arranged support member for selecting a vertical position of the cleaning members, the cleaning members each being selectively moveable relative to the frame portion;
 a mover configured to selectively cause movement of the frame member along the support member;
 a first motor associated with the first cleaning member for causing cleaning movement of the first cleaning member;
 a second motor associated with the second cleaning member for causing cleaning movement of the second cleaning member;
 a pressurized fluid storage tank supported on the vehicle;
 a plurality of nozzles situated near the cleaning members; and
 a valve assembly that is selectively controllable for directing fluid from the storage tank through the nozzles.

2. The machine of claim 1, wherein
 the mover comprises
  a hydraulic actuator and
  a propelling member that is at least partially moveable by the hydraulic actuator; and
 the frame portion comprises
  a follower that moves vertically responsive to movement of the propelling member.

3. The machine of claim 2, wherein
 the propelling member comprises a threaded rod;
 the hydraulic actuator selectively causes rotation of the threaded rod; and
 the follower includes a threaded surface that cooperates with the threaded rod to cause the frame portion to move vertically responsive to rotation of the threaded rod.

4. The machine of claim 1, wherein
 the first and second cleaning members each comprise at least one of an abrasive pad, a bristle brush or a buffing pad;
 the first and second cleaning members are independently rotatable relative to the frame portion;
 the first motor selectively causes rotation of the first cleaning member and;
 the second motor selectively causes rotation of the second cleaning member.

5. The machine of claim 4, comprising
 adjustment members that are configured to change an angle of orientation of an axis of rotation of each of the cleaning members, respectively, relative to the vehicle.

6. The machine of claim 1, wherein
 the vertically arranged support member comprises at least two upright beams;

the frame member is received between the two upright beams; and the frame member is configured to follow a path defined by the two upright beams.

7. The machine of claim 6, wherein the frame member comprises a generally rectangular support having side members that are situated for sliding along the upright beams.

8. The machine of claim 1, comprising a mounting plate that is selectively secured to the frame portion of the cleaning member assembly, the mounting plate including a tab that is received against the frame portion and a plurality of mounting sleeves each configured to receive and support a portion of a respective cleaning member.

9. The machine of claim 8, wherein the mounting plate tab is on one side of the plate and includes a hole configured to receive a pin for securing the tab to the frame portion; and the mounting sleeves are on an opposite side of the plate and each include a locking member for locking a corresponding portion of the respective cleaning member into a selected position within the mounting sleeve.

10. A method of cleaning dasher boards in an ice arena, comprising the steps of:

applying a cleaning solution to at least a portion of the dasher boards;

situating a cleaning machine near the portion of the dasher boards for positioning first and second cleaning members in contact with the portion of the dasher boards, the cleaning machine including a vehicle;

a carriage supported for movement with the vehicle, the carriage including at least one vertically arranged support member that is spaced from the vehicle, wherein the carriage is located transverse to a forward or reverse direction of the vehicle;

a cleaning member assembly including a frame portion that is supported by the carriage, the first and second cleaning members being supported by the frame portion, the frame portion having at least one frame member that is moveable along the vertically arranged support member for selecting a vertical position of the cleaning members, the cleaning members each being selectively moveable relative to the frame portion;

a mover configured to selectively cause movement of the frame member along the support member;

a first motor associated with the first cleaning member for causing cleaning movement of the first cleaning member;

a second motor associated with the second cleaning member for causing cleaning movement of the second cleaning member;

a pressurized fluid storage tank supported on the vehicle;

a plurality of nozzles situated near the cleaning members; and a valve assembly that is selectively controllable for directing fluid from the storage tank through the nozzles;

driving the cleaning machine at least partially around the ice arena with the cleaning members in a first vertical position for cleaning a first strip on a corresponding length of the dasher boards;

spraying fluid from the pressurized tank through the nozzles in a direction of a location where at least one of the cleaning members contacts the dasher boards;

adjusting a vertical position of the cleaning members, using the mover, into a second vertical position; and driving the cleaning machine at least partially around the ice arena with the cleaning members in the second vertical position for cleaning a second strip on the corresponding length of the dasher boards.

* * * * *

UNITED STATES PATENT AND TRADEMARK OFFICE
CERTIFICATE OF CORRECTION

| | | |
|---|---|---|
| PATENT NO. | : 9,254,071 B2 | Page 1 of 1 |
| APPLICATION NO. | : 13/749904 | |
| DATED | : February 9, 2016 | |
| INVENTOR(S) | : Brian Klanow | |

It is certified that error appears in the above-identified patent and that said Letters Patent is hereby corrected as shown below:

IN THE CLAIMS:

In claim 4, column 6, line 58: after "member" insert --;--

In claim 4, column 6, line 58: after "and" delete ";"

Signed and Sealed this
Twenty-third Day of August, 2016

Michelle K. Lee
*Director of the United States Patent and Trademark Office*